United States Patent [19]

Claeys et al.

[11] Patent Number: 4,853,521

[45] Date of Patent: Aug. 1, 1989

[54] SYSTEM FOR VERIFYING AND RECORDING DRUG ADMINISTRATION TO A PATIENT

[76] Inventors: Ronald W. Claeys, 1462 "I" St., Springfield, Oreg. 97477; Gary S. Decamp, 2595 Elysium, Eugene, Oreg. 97401

[21] Appl. No.: 138,171

[22] Filed: Dec. 28, 1987

[51] Int. Cl.⁴ ............................................. G06F 15/20
[52] U.S. Cl. .................................. 235/375; 235/462; 235/472; 364/413.01; 364/413.03; 364/567; 604/407
[58] Field of Search ............... 235/375, 376, 462, 463, 235/472; 364/413.01, 413.02, 413.03, 567; 604/407

[56] References Cited

U.S. PATENT DOCUMENTS

| | | | |
|---|---|---|---|
| 3,679,875 | 7/1972 | Rawson et al. | 235/375 |
| 3,831,006 | 8/1974 | Chaffin et al. | 235/375 |
| 3,848,112 | 11/1974 | Weichselbaum et al. | 235/375 |
| 4,053,951 | 10/1977 | Hudspeth et al. | 364/415 |
| 4,476,381 | 10/1984 | Rubin | 235/375 |
| 4,628,193 | 12/1986 | Blum | 235/472 X |

*Primary Examiner*—David L. Trafton
*Attorney, Agent, or Firm*—James D. Givnan, Jr.

[57] ABSTRACT

A progammable intelligent reader unit receives drug data from hand held and fixed scanners which read bar codes in place on syringes, ampules, vials, vaporizer controls, flow meters, etc., from or through which drugs are administrered to a patient. A scale additionally provides a data stream to the reader to provide a reader display of syringe weight before and after injection to enable the system user to immediately verify drug and dosage administered. A printer interfaced with the reader provides a time indicating anesthesia record. A program provides warnings, instructions and prompts for reader display to assist the system user.

15 Claims, 3 Drawing Sheets

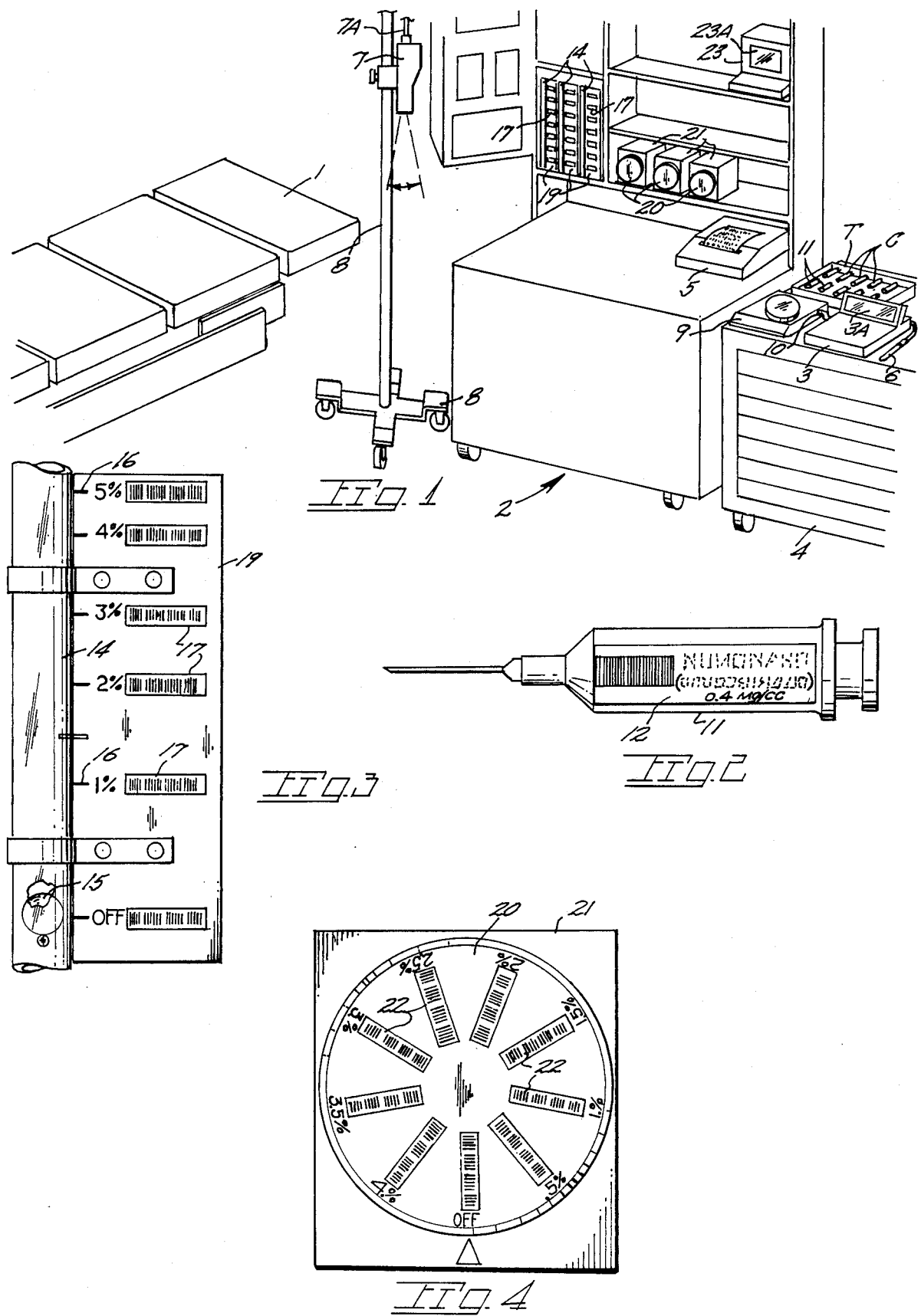

TO FIG. 5B

SYSTEM FOR VERIFYING AND RECORDING DRUG ADMINISTRATION TO A PATIENT

BACKGROUND OF THE INVENTION

The present invention pertains generally to a system for assuring the administration of the intended drug and dosage to a patient and making a record of same.

Common today is the practice of making handwritten entries of drugs and dosages administered to a patient. Such a practice is susceptible to mistakes particularly when entries on a log must necessarily be made at some time after administration in view of a busy operating room environment. The delayed log entries increase the chance that recollection or perception does not accurately serve the log keeper. Further, the compilation of a log results in interruptions of important tasks at hand and, for this reason, it ofttimes is put off with the chance of error being proportional to the length of delay. When the drugs involved are anesthetics any distraction, such as having to make a log entry, may contribute toward a mistake in drug use. Further, referral to dosage tables to verify a dosage is distractive and may result in accidental swapping of loaded syringes. The present system avoids the use of a keyboard by the end user.

SUMMARY OF THE PRESENT INVENTION

The present invention is embodied in a system which both verifies the drug and dosage administered and provides a data stream which is processed to provide a second review opportunity and ultimately a log.

A bar code is applied to each syringe to enable rapid verification of syringe contents by scanning of the syringe and the bar coded manufacturer's container. For convenience sake, the loaded syringes and manufacturer's drug containers are stored in paired fashion on a back table surgery/table adjacent to a scanner equipped reader. The reader affords a second check for the system user by displaying the drug name subsequent to passage of the syringe past a fixed scanner adjacent the patient. A swapped syringe triggers an audio signal from the reader upon being read by the scanner. Additionally displayed would be the dosage of drug injected which results from syringe tray weighing before and after the injection.

A scale sends weight data to the reader to complete the visual display i.e., the drug and the dosage of same administered. The reader is of the programmable type to also display prompts, warnings and instructions to the user. A hand held scanner enables reading of flow meter bar codes and bar coded settings of a vaporizer control to enable the data stream fed to the reader to reflect both gas and vapor rates.

The bar code intelligent reader serves to store data from the scanner or scanners and the scale for processing and later downloading to a computer or a printer to provide a log of all drug administrations with time notations. The scale transfers to the reader beginning and ending weights from which the reader can calculate the amount of drug administered.

Important objectives of the present invention include the provision of a real time data log of drugs, fluids, anesthetic gases and vapors administered to a patient; the provision of a system which accomplishes the aforementioned objective while decreasing the time the user devotes to record keeping; the provision of a system which greatly reduces the possibility of drug administration errors by providing the user a visual display of the drug name by the reader unit; the provision of a system wherein syringes are weighed, identified and re-weighed electronically to accurately verify the drug and dosage administered; the provision of a system for the administration of medications to patients using bar codes on containers, controls and conduits for vapors and gases; the provision of a system which permit the user to modify and vary the data as it enters a program by the use of several screen presentations, as for example, a screen for use in entering the patient's name, age, weight, attending medical personnel, etc.

BRIEF DESCRIPTION OF THE DRAWINGS

In the drawings:

FIG. 1 is a perspective view of the present system in place in a medical care facility;

FIG. 2 is a side elevational view of a hypodermic syringe identified with a bar code and name label;

FIG. 3 is a flow meter conduit segment equipped with bar codes;

FIG. 4 is a vaporizer control equipped with bar codes; and

DETAILED DESCRIPTION OF THE PREFERRED EMBODIMENTS

Figure 5A:
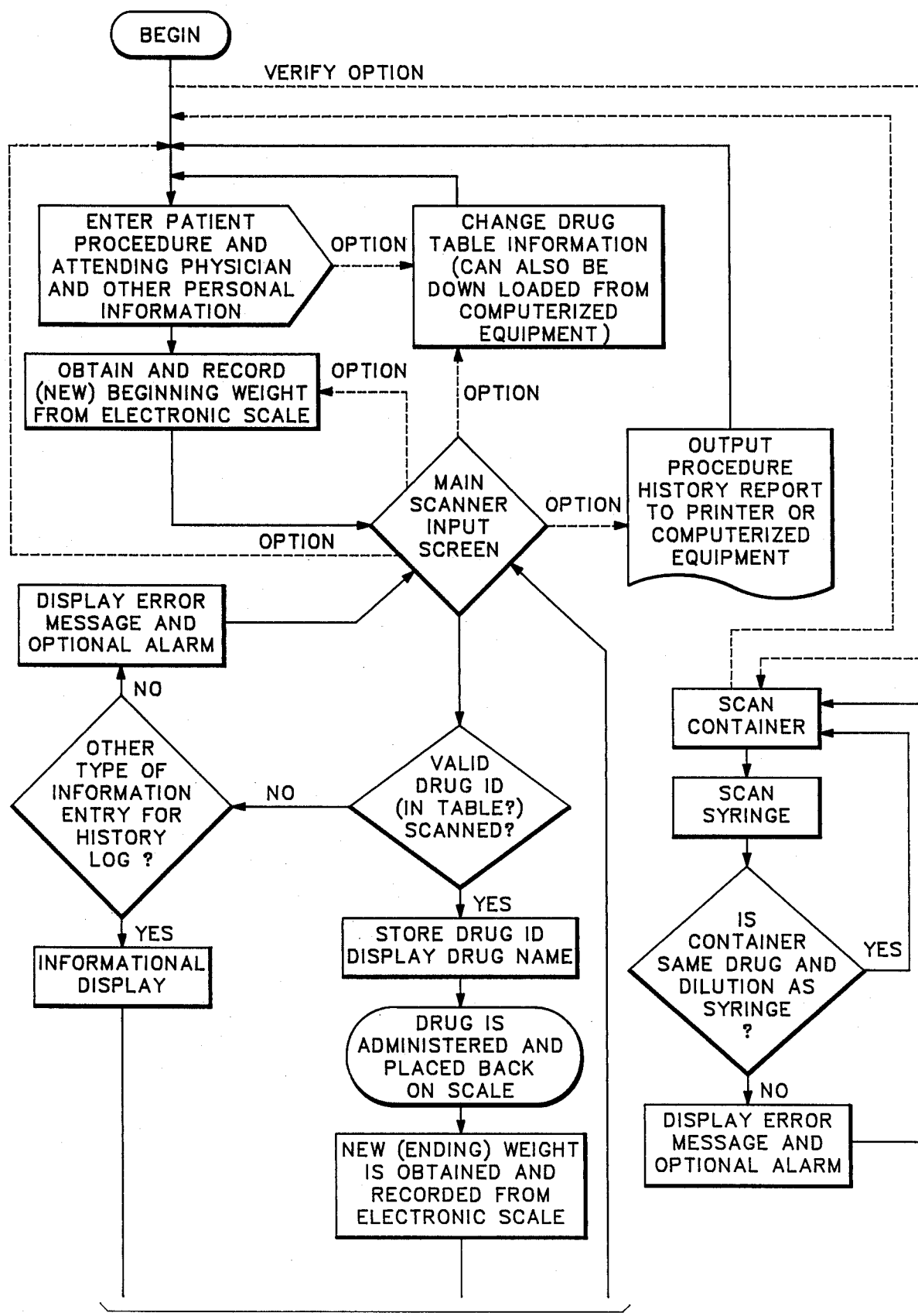
FIGS. 5A-5B are a flow chart of a program for the system.
Figure 5B:
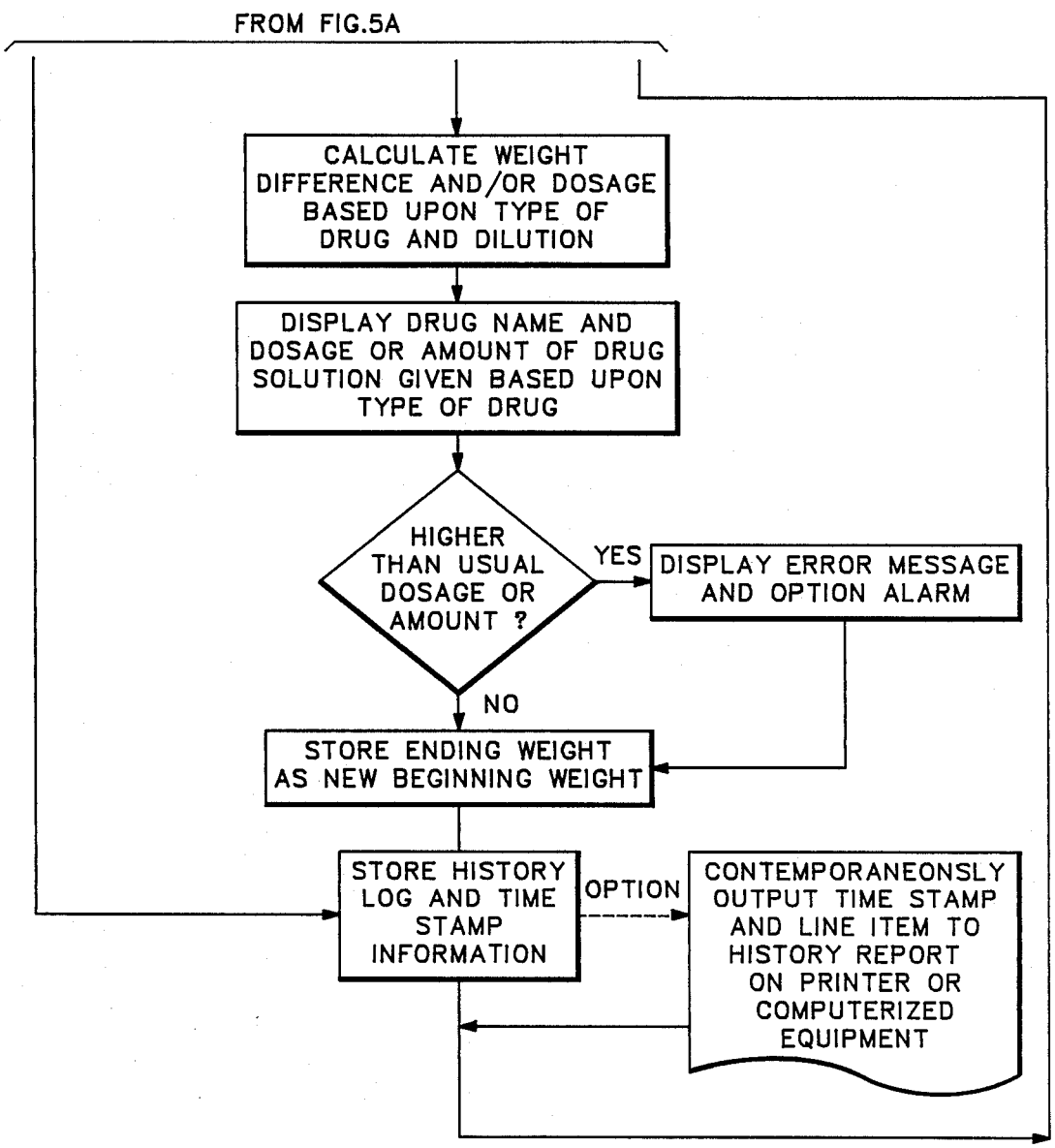

With continuing attention to the drawings wherein applied reference numerals indicate parts similarly hereinafter identified, the reference numeral 1 indicates a surgery bed for a patient being treated in an operating room. It is to be noted that the present system may also be utilized in other locations in a hospital and in types of other various medical facilities.

An anesthesia machine is indicated generally at 2. A reader 3 of the present system may be located on a back table 4 near machine 2. The reader is of the intelligent, programmable type capable of being programmed to prompt operators as well as collect data for subsequent transmission to a printer component at 5. In the preferred form of the system the reader is served by a hand held scanner or wand at 6 and a fixedly mounted or stationary scanner at 7 preferably of the non-contact type and supported in an elevated manner on an intravenous pole 8 or mounted on the anesthesia machine. Scanner 7 is of the moving beam type to read bar codes on syringes moved therepast by the system user immediately prior to injection of the syringe contents into a patient on bed 1. A cable 7A provides an interface with reader 3 having a visual display at 3A.

Additionally coupled to the reader 3 is an electronic balance 9, herein termed a scale, on which a tray T of drug bearing syringes is positioned as later described. The data from scale 9 i.e., tray weight before and after an injection, is fed to reader 3 via an interface cable 10.

A typical syringe at 11 in FIG. 2 is provided with a bar code label at 12 applied in any suitable manner which label preferably includes an alpha-numeric portion providing the generic name and tradename of the drug plus the dilution. Before a procedure, syringes on tray T are typically arranged in the order of use from left to right. To confirm syringe contents are as intended, each syringe and a bar coded container at C, such as a vial or ampule from the manufacturer, are scanned in sequence of intended use. For this purpose, tray T would also contain the manufacturer's container in alignment or otherwise paired with the appropriate syringe to enable convenient scanning at the start of a medical procedure. During a drug administration procedure, the syringe is drawn past scanner 7, the injection made after verifying by reference to the reader display. Return of the used syringe to tray T in place on the scale 9 will cause a new weight data transmission to be fed to reader 3 which will then display both the drug name and dosage for verification purposes with entry of same and the time into the reader memory. At this time, even should a wrong drug or dosage have been administered, it would in most instances be reversible where the drug had been discharged into intravenous tubing. The reader may be programmed to display a warning message or an audio or audio-visual signal when the dosage exceeds a certain amount.

In FIG. 3 we show a flow meter tube 14 having a bobbin 15 with scale indicia 16 on a placard 19 affixed to the tube. Typically the flow rate will cause bobbin 15 to move upwardly to enable flow rate determination. The present system may include the provision of flow meter bar code labels at 17 located at the noted liter flows to permit the system operator to enter flow rate data into the system by scanning the bar code label nearest the flow lifted bobbin. Again the entry would ultimately be on a time log record.

In FIG. 4, a valve handle 20 of a vaporizer control 21 which handle is shown as being rotatably set to determine flow through a vaporizer (not shown). Routinely used settings are represented by indices on the handle with each indices being a bar code label 22 to enable input of the handle setting (and hence vaporizer flow) from a scanner to reader 3. Such input to the reader ultimately appears on the timed data log. Any change in the setting of handle 20 would necessitate re-scanning of the repositioned handle to enter the time and new vaporizer setting.

An optional computer at 23 may be programmed with the intelligence necessary to conduct the present system and to maintain an electronic record of the information represented by the bar codes scanner for transfer to a permanent record at a later time. Toward this end a computer screen may be of the touch screen type at 23A.

The computer would be provided with several displays or screens, such as for example, a patient information screen to prompt entry of the patient's name and medical personnel names in attendance. Each drug to be administered would also be the subject of a screen. This data would be used to interact with other screens later during scanning.

Both the hand held scanner 6, the fixed scanner 7 and reader 3 may be of the type manufactured and sold by the INTERMEC Corporation. A suitable scale 9 is that scale termed Model FX-300 marketed by A&D Engineering, Inc.

The reader would have several screens or displays, the first of which would be used in verifying syringe bar code labels against the bar code label on manufacturer's ampule or vial. A second type of screen would be patient information screens for the entry of personal data of the patient and the names of attending personnel. The third screen type is for drugs and lists the drug name, dosages, calculations and warning messages. An optional screen would be for customizing reader tables to suit a specific user's requirements.

The record could be in the form of a timed printer output or electronically stored, transferred or displayed.

While we have shown but a few embodiments of the invention, it will be apparent to those skilled in the art that the invention may be embodied still otherwise without departing from the spirit and scope of the invention.

Having thus described the invention, what is claimed and desired to be secured by a Letters Patent is:

1. A system facilitating verification of medication administered to a patient and making a record of same, said system comprising,
    scanner means for reading bar codes,
    a scale,
    bar code bearing medication containers stored in place on said scale before and after drug administration to the patient, and
    a bar code reader unit with display interfaced with said scale and scanner means, said unit being of the intelligent programmable type and capable of making a record and further capable of displaying instructions and data from bar codes read by said scanner means and weight data from said scale.

2. The system claimed in claim 1 additionally including a computer interfaced with said bar code reader unit.

3. The system claimed in claim 1 additionally including a printer component interfaced with said reader unit.

4. The system claimed in claim 3 wherein said scanner means includes a fixed non-contact scanner and a hand held scanner.

5. The system claimed in claim 4 additionally including a vaporizer valve control having bar codes thereon indicating valve control settings.

6. The system claimed in claim 4 additionally including a flow meter with an upright flow meter conduit segment with bobbin, said flow meter having bar codes located at different points to enable scanning of a bar code proximate the flow elevated bobbin along said conduit segment.

7. A method of verifying administration of a medication to a patient consisting of the steps of,
    placing a bar coded syringe on a scale interfaced with an electronic reader unit having a display,
    manually moving the bar coded syringe immediately before drug administration past a scanner also interfaced with the reader unit for scanning of the bar code on the syringe,
    observing the reader unit for drug names,
    replacing the syringe on the scale, and
    observing the reader unit display for verification of the drug name and dosage administered.

8. The method claimed in claim 7 including the preliminary step of electronically scanning the syringe carried bar codes and the bar code on a manufacturer's drug container to verify the same drug is in both syringe and container.

9. The method claimed in claim 7 additionally including the step of moving a hand held electronic scanner past a bar code affixed to a vaporizer control and corresponding to a control setting.

10. The method claimed in claim 7 additionally including the step of moving a hand held electronic scanner past a flow meter having a bobbin equipped conduit segment and specifically past a bar code affixed at a point along said conduit segment.

11. A system facilitating verification of medication administered to a patient, said system comprising,
    scanner means for reading bar codes.

a scale, bar code bearing medication containers for placement on said scale before and after drug administration of their contents to the patient, and a bar code reader unit interfaced with said scale and scanner means, said unit being of the intelligent programmable type for displaying both instructions, data and warning messages from bar codes read by the scanner and input from said scale.

12. The system claimed in claim 11 wherein said scanner means includes a fixed non-contact scanner.

13. The system claimed in claim 12 wherein said scanner means includes a hand held scanner.

14. The system claimed in claim 13 additionally including a valve control of a vaporizer, said control having bar codes thereon corresponding to settings of the vaporizer.

15. The system claimed in claim 13 additionally including a flow meter with an upright conduit segment with bobbin, bar codes located at different points along the segment to enable scanning of a bar code proximate the flow elevated bobbin.

* * * * *